United States Patent [19]

Oki et al.

[11] 4,373,094

[45] Feb. 8, 1983

[54] ANTHRACYCLINE DERIVATIVES

[75] Inventors: Toshikazu Oki, Yokohama; Yasue Matsuzawa, Fujisawa; Tomoyuki Ishikura, Chigasaki; Tomio Takeuchi; Hamao Umezawa, both of Tokyo, all of Japan

[73] Assignee: Sanraku-Ocean Co., Ltd., Tokyo, Japan

[21] Appl. No.: 288,072

[22] Filed: Jul. 29, 1981

[30] Foreign Application Priority Data

Aug. 1, 1980 [JP] Japan .................................. 55-106522

[51] Int. Cl.³ ........................ A61K 31/71; C07H 15/24
[52] U.S. Cl. ....................................... 536/6.4; 424/180

[58] Field of Search ...................................... 536/17 A

[56] References Cited

U.S. PATENT DOCUMENTS 4,127,714 11/1978 Umezawa et al. ................. 536/17 A
4,316,011 2/1982 Oki ..................................... 536/17 A

*Primary Examiner*—Johnnie R. Brown
*Attorney, Agent, or Firm*—Jordan and Hamburg

[57] ABSTRACT

New anthracycline compounds, 2-hydroxy-aclacinomycins M, N, S and T having potent antitumor activity and low toxicity, and the processes for the preparation thereof from 2-hydroxy-aclacinomycin A by reduction or acid hydrolysis are disclosed.

5 Claims, No Drawings

ANTHRACYCLINE DERIVATIVES

BACKGROUND OF THE INVENTION

(1) Field of the Invention

The present invention relates to novel anthracycline compounds and to processes for their preparation. More particularly, the present invention relates to novel anthracycline compounds designated 2-hydroxy-aclacinomycins M, N, S and T, to processes for the preparation thereof by reduction or acid hydrolysis of 2-hydroxy-aclacinomycin A, and to the methods for their recovery and purification.

(2) Description of the Prior Art

A number of anthracycline glycosides have been found in the culture medium of Streptomyces, and are described in prior literature. Among them, daunomycin and adriamycin have already been clinically applied for human cancers.

Rhodomycinones, iso-rhodomycinone and rhodomycin-related antibiotics are described in Chem. Ber. 88, 1792–1818 (1955); Chem. Ber. 101, 1341–1348 (1968); J. Med. Chem., 20, 957–960 (1977); Pharmacie 27, 782–789 (1972); Zeit. Allg. Mikrobiol., 14, 551–558 (1974); Tetrahed. Lett. No. 38, 3699–3702 (1973); Folia Microbiol., 24, 293–295 (1979); and J. Antibiotics, 32, 420 (1979).

Aclacinomycin A is disclosed in U.S. Pat. No. 3,988,315 and by Oki et al. in J. Antibiotics 28, 830 (1975) and 32, 791–812 (1979). Cinerubins A and B are disclosed in U.K. Pat. No. 846,130, U.S. Pat. No. 3,864,480, Keller-Schierlein et al., "Antimicrobial Agents and Chemotherapy," page 68 (1970), Chemical Abstracts 54, 1466i (1960) and J. Antibiotics 28, 830 (1975).

Further illustrative and summary disclosures of anthracycline antibiotics can be located in Index of Antibiotics from Actinomycetes, Hamao Umezawa, Editor-in-Chief, University Park Press, State College, Pennsylvania, U.S.A. (1967) as follows:

| Antibiotics | Page numbers |
|---|---|
| Aclacinomycins A and B | 101–102 |
| Adriamycin | 122 |
| Carminomycin I | 225 |
| Galirubins S–D | 405–408 |
| Rhodomycins X–Y | 879–880 |
| β-Rhodomycins | 881–885 |
| γ-Rhodomycins | 886–892 |
| Steffimycin | 945 |

The textbook, Antibiotics, Volume 1, Mechanism of Action, edited by David Gottlieb and Paul D. Shaw, Springer-Verlag New York, Inc., N.Y. (1967) at pages 190–210 contains a review by A. Dimarco entitled "Daunomycin and Related Antibiotics."

Information Bulletin, No. 10, International Center of Information of Antibiotics, in collaboration with WHO, Dec. 1972, Belgium, reviews anthracyclines and their derivatives.

SUMMARY OF THE INVENTION

This invention relates to anthracycline derivatives and acid addition salts thereof having the general formula:

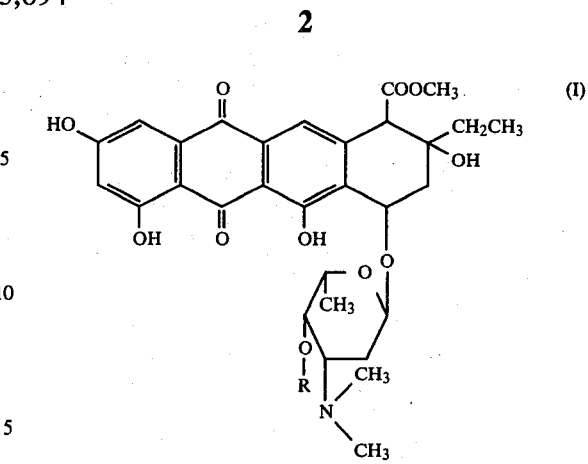

wherein R represents a hydrogen atom, or a sugar chain moiety of the formula:

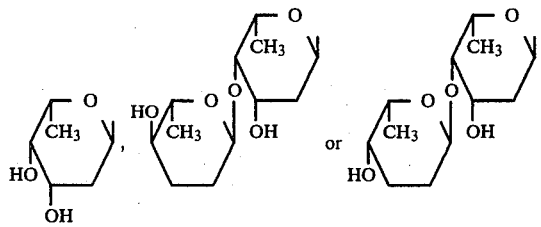

DETAILED EXPLANATION OF THE INVENTION

The present invention relates to antitumor anthracycline antibiotics and more particularly to anthracycline derivatives and acid addition salts thereof having the following general formula I:

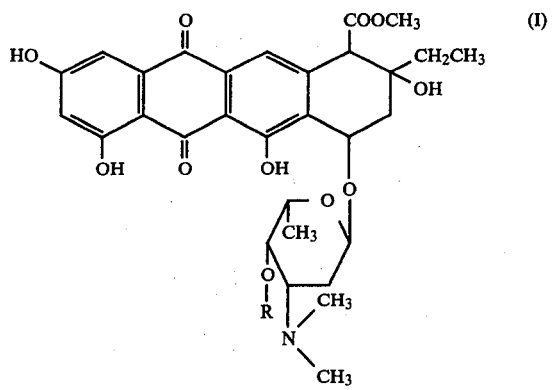

wherein R represents a hydrogen atom, or a sugar chain moiety of the formula:

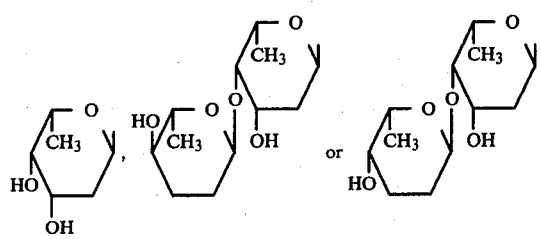

A novel antitumor anthracycline antibiotic, 2-hydroxy-aclacinomycin A, of the following formula II:

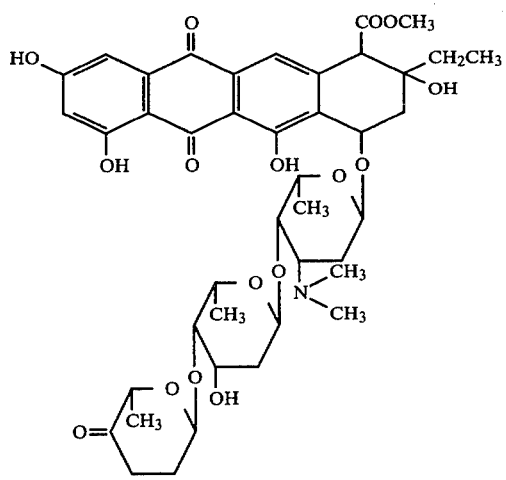

has been found by the present inventors and disclosed in U.S. patent application Ser. No. 184,518.

It has been found that the compound of the formula I remarkably inhibits the growth and nucleic acids synthesis of cultured mouse leukemia L1210 cells at a low concentration and is possibly used as an antitumor agent, after a long intensive study to try to obtain much better antitumor substances than the above-mentioned antibiotic, 2-hydroxy-aclacinomycin A. The present invention is based on this discovery.

The compounds of the present invention may be obtained by reduction or hydrolysis of the compound of the formula II or acid addition salts thereof, in which the reaction process is known per se. For example, 2-hydroxy-aclacinomycin A is treated with a reducing reagent such as sodium boron hydride or lithium aluminum hydride under appropriate reaction conditions to reduce the carbonyl group of the terminal sugar moiety, cinerulose A. The sugar moiety is converted to amicetose or rhodinose and 2-hydroxy-aclacinomycin M, in which R of the general formula I is a group of the formula:

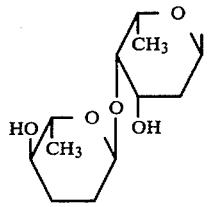

or 2-hydroxy-aclacinomycin N, in which R of the general formula I is a group of the formula:

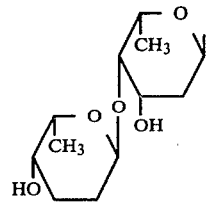

is obtained. Furthermore, 2-hydroxy-aclacinomycin A, 2-hydroxy-aclacinomycin M or 2-hydroxy-aclacinomycin N is subjected to mild hydrolysis with 0.05–0.5 N hydrochloric acid or sulfuric acid to remove the terminal sugar or the two terminal chained sugars. By the treatment, 2-hydroxy-aclacinomycin S, in which R of the general formula I is a group of the formula:

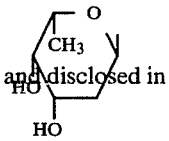

or 2-hydroxy-aclacinomycin T, in which R of the general formula I is a hydrogen atom is obtained. 2-Hydroxy-aclacinomycin T may also be produced from 2-hydroxy-aclacinomycin S that is obtained according to the above-mentioned process by a mild hydrolysis further to remove the terminal sugar moiety. The compounds thus obtained of the general formula I may be purified according to the known isolation and purification processes that are usually used in the art of anthracycline antibiotics.

The compounds of the present invention are basic and form addition salts with various kinds of inorganic and organic acids. Namely, the compounds of the general formula I may be obtained as addition salts with an acid such as hydrochloric acid, sulfuric acid, phosphoric acid, oxalic acid, nitric acid, acetic acid, propionic acid, maleic acid, oleic acid, palmitic acid, citric acid, succinic acid, tartaric acid, furmaric acid, glutamic acid, pantothenic acid, laurylsulfonic acid, benzenesulfonic acid and naphthalenesulfonic acid by the known processes for formation of salt from free bases. A representative process for salt formation consists of treating the compound of free base form of the present invention with the above-mentioned acid in an appropriate solvent and obtaining the reaction product by freeze-drying or recovering it by precipitation with a solvent in which the corresponding salt is rarely dissolved.

Physicochemical properties of the compounds of the present invention are given in Table 1.

TABLE 1

| Compound | 2-Hydroxy-aclacinomycin M | 2-Hydroxy-aclacinomycin N | 2-Hydroxy-aclacinomycin S | 2-Hydroxy-aclacinomycin T |
| --- | --- | --- | --- | --- |
| Appearance | Yellowish brown powder | Yellowish brown powder | Yellowish brown powder | Yellowish brown powder |
| Molecular weight | 829.9 | 829.9 | 715.7 | 585.6 |
| Elementary analysis | As $C_{42}H_{55}NO_{16}$ | As $C_{42}H_{55}NO_{16}$ | As $C_{36}H_{45}NO_{14}$ | As $C_{30}H_{35}NO_{11}$ |
| Observed | C 60.34 | C 60.30 | C 60.28 | C 61.14 |
|  | H 6.87 | H 6.85 | H 6.51 | H 6.41 |
|  | N 1.63 | N 1.71 | N 1.93 | N 2.32 |
| Calculated | C 60.79 | C 60.79 | C 60.41 | C 61.53 |
|  | H 6.68 | H 6.68 | H 6.34 | H 6.02 |
|  | N 1.69 | N 1.69 | N 1.96 | N 2.39 |

TABLE 1-continued

| Compound | 2-Hydroxy-aclacinomycin M | 2-Hydroxy-aclacinomycin N | 2-Hydroxy-aclacinomycin S | 2-Hydroxy-aclacinomycin T |
|---|---|---|---|---|
| Melting point (°C.) | 168–170 | 167–169 | 170–172 | 169–171 |
| $(\alpha)_D^{23}$ (in MeOH) | +123° (c 0.04) | +103° (c 0.04) | +140° (c 0.04) | +299° (c 0.01) |
| Ultraviolet and visible absorption spectra $\lambda_{max}^{90\% MeOH}$ nm($E_{1cm}^{1\%}$) | 222(390) 256(235) 294(210) 440(116) 525s(38) | 223(381) 256(227) 294(204) 440(113) 520s(37) | 222(423) 256(270) 295(233) 450(125) 510s(65) | 222(515) 256(330) 297(278) 455(148) 510s(90) |
| Infrared absorption spectrum cm$^{-1}$, KBr tablet | 1730, 1670 1620, 1250 1010, 1000 | 1735, 1675 1620, 1250 1000 | 1735, 1675 1620, 1255 1010, 995 | 1730, 1670 1620, 1250 1010, 980 |

Solubilities of the compounds of the present invention, 2-hydroxy-aclacinomycins M, N, S and T, are almost similar. They are soluble in acidic water, methanol, ethanol, n-butanol, acetone, ethyl acetate, chloroform, benzene, toluene, dimethylsulfoxide and methyl cellosolve, slightly soluble in water, ether and n-hexane. The color of the solutions, when they are dissolved, is yellow or yellowish brown, which is changed to violet in alkaline solution.

Chemical structures of the compounds of the present invention were determined by IR, UV, NMR and elementary analysis, and also by the instrumental analysis of aglycones that are formed by the hydrolysis of the compounds of the present invention. Namely, IR absorption spectra showed absorption peaks of methoxy carbonyl group at 1730–1735 cm$^{-1}$, quinone carbonyl group at 1670–1675 cm$^{-1}$, hydrogen bond-type quinone carbonyl group at 1620 cm$^{-1}$ and sugar ether group at 1010 cm$^{-1}$. The present compounds were confirmed to have the same chromophore as 2-hydroxy-aclacinomycin A (Japan patent application No. Showa 55-92880) has, because they have a maximum absorption at 440–455 nm in the visible absorption spectra. 2-Hydroxy-aclacinomycins M, N, S and T were dissolved in 0.1 N hydrochloric acid and heated at 85° C. for 30 minutes, respectively. Each aglycone thus formed was isolated, and the IR, UV, NMR and Mass spectra and melting point were measured. The values were in accordance with those of 2-hydroxy-aklavinone (Japan patent application No. Showa 54-115520), which assures that the compounds of the present invention have the same aglycone as 2-hydroxy-aclacinomycin A has.

The sugar moieties of the compounds of the present invention were analized by silica gel thin-layer chromatography (Merck Co. 60F$_{254}$, Solvent system; n-butanol:acetic acid:water, 4:1:1) with the neutralized and concentrated water-soluble fraction of the hydrolysate. 2-Hydroxy-aclacinomycins M and N gave 3 kinds of sugars, and 2-hydroxy-aclacinomycin S provided 2 kinds of sugars. From 2-hydroxy-aclacinomycin T, only one sugar was detected. Comparison of these sugars with authentic sugar samples obtained from MA144 M1 and MA144 N1 (J. Antibiotics 32, 801–819, 1979) showed that 3 kinds of sugars from 2-hydroxy-aclacinomycin M were amicetose, 2-deoxy-fucose and rhodosamine, and that 3 kinds of sugars from 2-hydroxy-aclacinomycin N were rhodinose, 2-deoxy-fucose and rhodosamine. It was also shown that 2 kinds of sugars from 2-hydroxy-aclacinomycin S were 2-deoxy-fucose and rhodosamine and that a sugar from 2-hydroxy-aclacinomycin T was rhodosamine.

Accordingly, it has been found that the compounds of the present invention are novel substances having the structure of the formula I which are chemically derived from the new anthracycline antibiotic, 2-hydroxy-aclacinomycin A.

The compounds of the present invention inhibited the growth and nucleic acids synthesis of cultured mouse leukemia L1210 cells at a low concentration remarkably. The L1210 cells were cultivated at 37° C. overnight and transferred to RPMI (Roswell Park Memorial Institute) 1640 medium containing 20% calf serum at their exponential growth phase so as to give a cell concentration of 4×10$^4$ cells/ml. The compounds of the present invention were added to the medium at a concentration of 0.02–0.5 μg/ml. Incubation was performed in a CO$_2$-incubator at 37° C. for 3 days and then the number of living cells was counted.

Independently of the above-mentioned experiment, the compounds of the present invention were added to an about 5×10$^5$ cells/ml L1210 cell suspension in RPMI 1640 medium containing 10% calf serum at a concentration of 0.02–2.5 μg/ml. After 15 minutes, $^{14}$C-uridine (0.05 μCi/ml) or $^{14}$C-thymidine (0.05 μCi/ml) was added to the suspension and pulse-labeling was carried out at 37° C. for 60 minutes. The reaction was stopped by addition of a cold 10% trichloroacetic acid solution and an acid-insoluble fraction was precipitated. The precipitate was washed with a cold 5% trichloroacetic acid and the radioactivity was measured. Table 2 shows the concentrations of 50% inhibition for cell growth and for incorporation of radioactivity on the basis of the control value.

TABLE 2

| | Antitumor activity 50% Inhibitory concentration (μg/ml) | | |
|---|---|---|---|
| Compound | Growth inhibition after 24 hours | $^{14}$C—Thymidine (Inhibition of DNA synthesis | $^{14}$C—Uridine (Inhibition of RNA synthesis |
| 2-hydroxy-aclacinomycin M | 0.08 | 1.2 | 0.1 |
| 2-hydroxy-aclacinomycin N | 0.095 | 1.2 | 0.18 |
| 2-hydroxy-aclacinomycin S | 0.70 | 5.0 | 1.3 |
| 2-hydroxy-aclacinomycin T | 0.46 | 2.6 | 1.0 |
| 2-hydroxy-aclacinomycin A | 0.15 | 0.9 | 0.14 |

Accordingly, it has been found that the novel compounds of the present invention, 2-hydroxy-aclacinomycins M, N, S and T, have an antitumor effect on L1210 leukemia cells.

The present invention is further illustrated by the following examples.

EXAMPLE 1

2-Hydroxy-aclacinomycin A (400 mg) was dissolved in 120 ml of chloroform and 18 ml of ethanol. To the solution, 40 mg of sodium boron hydride was added and the mixture was stirred at a room temperature for 45 minutes. After the reaction was completed, 100 ml of chloroform and 100 ml of distilled water was added to decompose the excess of sodium boron hydride. The chloroform layer was washed with $10^{-2}$ M ethylenediamine tetraacetate (EDTA), pH 7.0, and with distilled water twice, dried with anhydrous sodium sulfate, and then evaporated to dryness under reduced pressure. The residue obtained (400 mg) was spotted onto a silica gel plate for preparative layer chromatography (Merck Co. $PF_{254}$) in a linear manner. Development was carried out with a solvent system of chloroform:methanol (100:15, V/V). The silica gel layer at Rf 0.29 corresponding to 2-hydroxy-aclacinomycin M and at Rf 0.21 corresponding to 2-hydroxy-aclacinomycin N was peeled off respectively. Each gel was treated with a mixture of chloroform:methanol:aqueous ammonia (100:15:0.2) for extraction. Precipitation with n-hexane from each concentrated extract provided 230 mg of 2-hydroxy-aclacinomycin M and 76 mg of 2-hydroxy-aclacinomycin N as a yellowish brown powder, respectively.

EXAMPLE 2

2-Hydroxy-aclacinomycin M (170 mg) obtained according to Example 1 was dissolved in 200 ml of 0.05 N hydrochloric acid and hydrolyzed at a room temperature for 5 hours. The hydrolysate was neutralized to pH 7.5 with diluted aqueous alkali solution and treated with 200 ml of chloroform for extraction 4 times. The chloroform extracts were combined, dried with anhydrous sodium sulfate, and then evaporated to dryness under reduced pressure. The residue obtained (160 mg) was subjected to preparative layer chromatography on a silica gel plate (solvent system; chloroform:methanol, 100:15). The silica gel layer at Rf 0.09 corresponding to 2-hydroxy-aclacinomycin S and at Rf 0.05 corresponding to 2-hydroxy-aclacinomycin T was peeled off and treated with a mixture of chloroform:methanol:aqueous ammonia (100:15:0.2) for extraction, respectively. Each extract was concentrated and n-hexane was added to precipitate each extracted reaction product, respectively. 2-Hydroxy-aclacinomycin S (46 mg) and 2-hydroxy-aclacinomycin T (7 mg) were obtained as a yellowish brown powder.

EXAMPLE 3

2-Hydroxy-aclacinomycin N (60 mg) obtained according to Example 1 was dissolved in 100 ml of 0.05 N hydrochloric acid and hydrolyzed at a room temperature for one hour. The hydrolysate was neutralized to pH 7.5 with diluted aqueous alkali solution and treated with 120 ml of chloroform for extraction. The chloroform layers were combined, dried with anhydrous sodium sulfate, and evaporated to dryness in vacuo. The residue obtained (58 mg) was isolated and purified in the same manner as in Example 2. 2-Hydroxy-aclacinomycin S (27 mg) and 2-hydroxy-aclacinomycin T (2 mg) were obtained as a yellowish brown powder.

EXAMPLE 4

2-Hydroxy-aclacinomycin A (100 mg) was dissolved in 100 ml of 0.5 N hydrochloric acid and hydrolyzed at room temperature for 10 minutes. 2-Hydroxy-aclacinomycins S (9 mg) and T (23 mg) were obtained as a yellowish brown powder by the same isolation and purification procedure as described in Example 2.

EXAMPLE 5

2-Hydroxy-aclacinomycin S (27 mg) obtained in the same manner as in Example 2 was dissolved in 30 ml of 0.5 N hydrochloric acid and hydrolyzed at a room temperature for one hour. 2-Hydroxy-aclacinomycin T (12 mg) was obtained as a yellowish brown powder by the same isolation and purification procedure as described in Example 2.

The following example shows the preparation of 2-hydroxy-aclacinomycin A that is used as the starting material in the present invention.

EXAMPLE

A 100 ml portion of a medium containing 1.5% soluble starch, 1% glucose, 1% soy bean meal, 0.1% yeast extract, 0.3% sodium chloride, 0.1% dipotassium hydrogen phosphate ($K_2HPO_4$), 0.1% $MgSO_4.7H_2O$, 0.007% $CuSO_4.5H_2O$, 0.001% $FeSO_4.7H_2O$, 0.0008% $MnCl_2.4H_2O$ and 0.0002% $ZnSO_4.7H_2O$, pH 7.4, was sterilized in a 500 ml-Erlenmeyer flask and inoculated with a roop of *Streptomyces galilaeus* KE 303 grown on a slant agar medium. The inoculated medium was incubated with shaking on a rotary shaker at 28° C. for 48 hours to give a seed culture. A 50 ml-portion of a fermentation medium containing the same constituents as described above except 2% soy bean meal and 0.2% yeast extract was sterilized in a 500 ml-Erlenmeyer flask and inoculated with 1 ml of the seed culture. A total of 1000 flasks containing the inoculated medium was incubated with shaking on a rotary shaker (210 R.P.M.) at 28° C. for 17 hours. To the culture was added 0.5 ml of 2 mg/ml methanol solution of 2-hydroxy-aklavinone (at a final concentration of 20 μg/ml and 1.0 g in total) that was obtained according to the process described in U.S. patent application Ser. No. 184,518. Incubation was continued for a further 24 hours.

In order to estimate the transformation ratio of 2-hydroxy-aclacinomycin A at the end of fermentation, 5 ml of a mixture of chloroform and methanol (3:2) was added to 5 ml of the cultured broth taken for a sampling test and the transformation product was extracted to a chloroform layer by stirring the mixture with a Thermomixer. The chloroform layer was evaporated to dryness and the residue was dissolved in 0.2 ml of chloroform. A 20 μl-portion of the solution was spotted to a silica gel plate for thin-layer chromatography (Merck Co. $F_{254}$). Thin-layer chromatography was carried out with a solvent system of chloroform:methanol:conc. aqueous ammonia (50:10:0.5). After the developed plate was air-dried, spots of 2-hydroxy-aclacinomycin A at Rf 0.51 and residual 2-hydroxy-aklavinone at Rf 0.30 were quantitatively determined with Shimazu Chromatoscanner Type CS-910. More than 90% of 2-hydroxy-aklavinone was transformed and a yield of 2-hydroxy-aclacinomycin A was 680 mg in total.

Cultured broths (50 l in total) were combined and cells were collected by centrifugation. The transformation product was extracted with 8 liters of acetone. After the acetone extract was evaporated in vacuo to a ⅓ volume, the product was reextracted with 3 liters of chloroform. Evaporation of the collected chloroform layer to dryness yielded a crude extract. The crude extract of transformation product was dissolved in 50 ml of methanol. After the insoluble residue was removed by centrifugation, the supernatant solution was applied to a Sephadex LH-20 colum (φ5.0×40 cm) and eluted with methanol. The first yellow-colored fractions were collected and concentrated to dryness. The residue was dissolved in a small volume of chloroform. The solution was applied onto 50 sheets of silica gel plate for preparative layer chromatography (Merck Co., Kieselgel 60 PF$_{254}$) in the manner that the spot was along a linear line with a 1.5 cm-distance from the lower end of the plate. Development was carried out with a solvent system of chloroform:methanol:conc. aqueous ammonia (50:10:0.3). Silica gel of a main band of 2-hydroxy-aclacinomycin A around Rf 0.68 was peeled off and treated with about 200 ml of chloroform:methanol mixture (4:1) for extraction. The extract was washed with an appropriate volume of distilled water, and the chloroform layer was collected and concentrated to dryness. The residue was dissolved again in a small amount of chloroform. The solution was applied in linear manner onto 25 sheets of silica gel plate for preparative layer chromatography in the same way as described above and developed with a solvent system of chloroform:methanol:glacial acetic acid (80:10:0.5). Silica gel of yellow colored band at Rf 0.22 and treated with about 200 ml of a mixture of chloroform:methanol:conc. aqueous ammonia (40:10:0.5) for extraction. The extract was washed with distilled water and the collected chloroform layer was concentrated to give 388 mg of purified preparation. Then, the preparation thus obtained was dissolved in 30 ml of methanol and applied to a Sephadex LH-20 column (φ5.0×40 cm). The corresponding fractions were collected and concentrated to dryness. The residue was dissolved in 20 ml of 0.2 M acetate buffer solution (pH 3.5). After a small amount of insoluble matter was removed by centrifugation, the supernatant solution was neutralized with 4 N NaOH at a low temperature in an ice bath and treated with chloroform for extraction. The chloroform extract was washed with 0.01 M EDTA (pH 6.0) and with water, dried with anhydrous sodium sulfate and concentrated in vacuo. An excess volume of n-hexane was added to the concentrate to produce orange precipitate, which was collected by filtration and dried in vacuo to give 293 mg of pure 2-hydroxy-aclacinomycin A.

What is claimed is:

1. Anthracycline derivatives and acid addition salts thereof having the general formula:

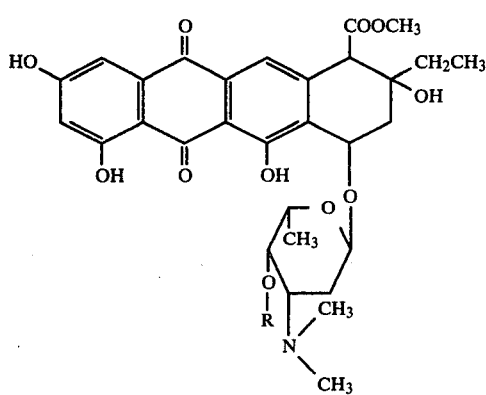

wherein R represents a hydrogen atom, or a sugar chain moiety of the formula:

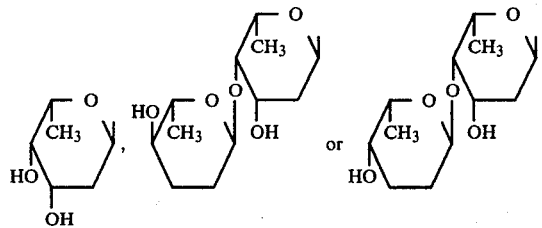

2. Anthracycline derivatives and acid addition salts thereof according to claim 1 in which the compound is 2-hydroxy-aclacinomycin N of the formula I wherein R represents a group of the formula:

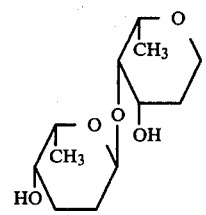

3. Anthracycline derivatives and acid addition salts thereof in which the compound is 2-hydroxy-aclacinomycin M having the general formula:

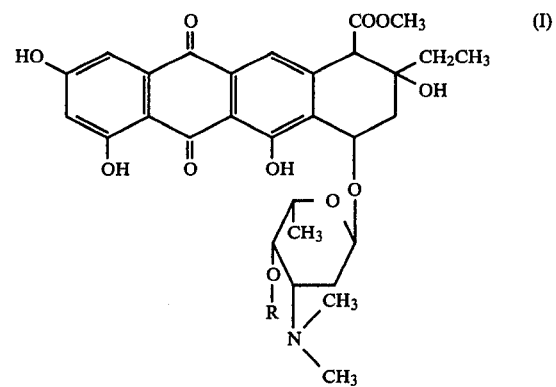

wherein R represents a group of the formula:

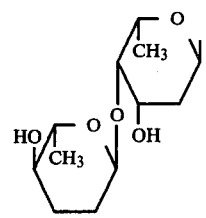

4. Anthracycline derivatives and acid addition salts thereof in which the compound is 2-hydroxy-aclacinomycin S having the general formula:

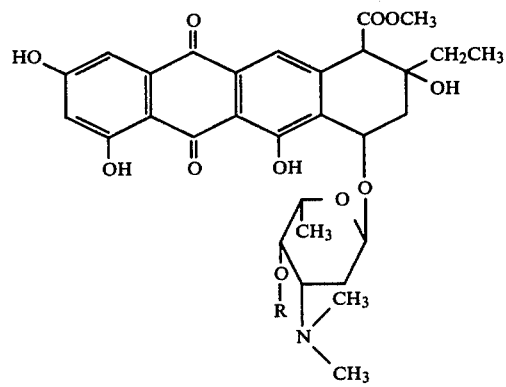
wherein R represents a group of the formula:
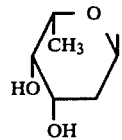
5. Anthracycline derivatives and acid addition salts thereof in which the compound is 2-hydroxy-aclacinomycin T having the general formula:
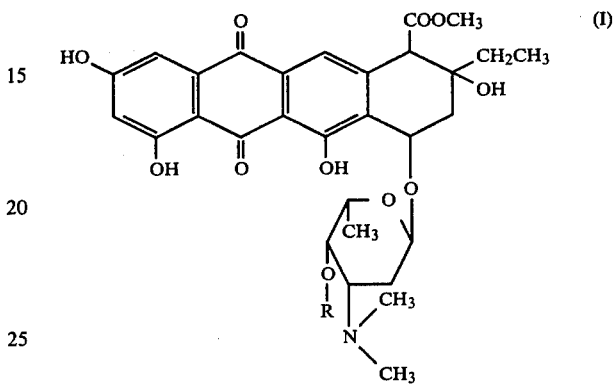
wherein R represents a hydrogen atom.
* * * * *